(12) United States Patent  
Ravishankar et al.

(10) Patent No.: US 9,227,886 B2
(45) Date of Patent: Jan. 5, 2016

(54) POLYMERIZATION PROCESS

(71) Applicants: Periagaram S. Ravishankar, Kingwood, TX (US); Aaron H. Reed, Zachary, LA (US)

(72) Inventors: Periagaram S. Ravishankar, Kingwood, TX (US); Aaron H. Reed, Zachary, LA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 561 days.

(21) Appl. No.: 13/650,971

(22) Filed: Oct. 12, 2012

(65) Prior Publication Data

US 2014/0107386 A1   Apr. 17, 2014

(51) Int. Cl.
*C08F 2/06* (2006.01)
*C08F 4/68* (2006.01)
*C07C 2/06* (2006.01)
*C08F 210/18* (2006.01)
*C08F 210/16* (2006.01)

(52) U.S. Cl.
CPC ............... *C07C 2/06* (2013.01); *C08F 210/18* (2013.01)

(58) Field of Classification Search
CPC .............. C07C 2/06; C08F 2/06; C08F 2/04; C08F 210/18

USPC ................. 585/506; 526/72, 73, 282, 336
See application file for complete search history.

(56) References Cited

U.S. PATENT DOCUMENTS

| 2,858,902 | A | * | 11/1958 | Cottle | 95/143 |
| 4,540,753 | A | | 9/1985 | Cozewith et al. | |
| 7,119,157 | B2 | | 10/2006 | Kim et al. | |
| 2006/0160966 | A9 | * | 7/2006 | Datta et al. | 526/126 |
| 2011/0172375 | A1 | * | 7/2011 | Yeh et al. | 526/74 |

FOREIGN PATENT DOCUMENTS

| EP | 0 748 825 | 12/1996 |
| EP | 1 659 137 | 5/2006 |

* cited by examiner

*Primary Examiner* — Fred M Teskin

(57) ABSTRACT

The present invention relates to a polymerization process of producing ethylene-alpha-olefin polymer. The polymerization process comprises supplying at a feed temperature a feed containing ethylene, at least one alpha-olefin and optionally, a diene in a solvent, the solvent is supplied at a solvent feed rate; supplying at a catalyst feed rate a catalyst to a reactor, and contacting the feed with the catalyst to produce a reaction mixture containing the polymer. The present invention also relates to processes for improving the energy utilization of polymerization processes, wherein the process comprises decreasing the feed temperature, decreasing the solvent feed rate, and decreasing the catalyst feed rate.

24 Claims, 1 Drawing Sheet

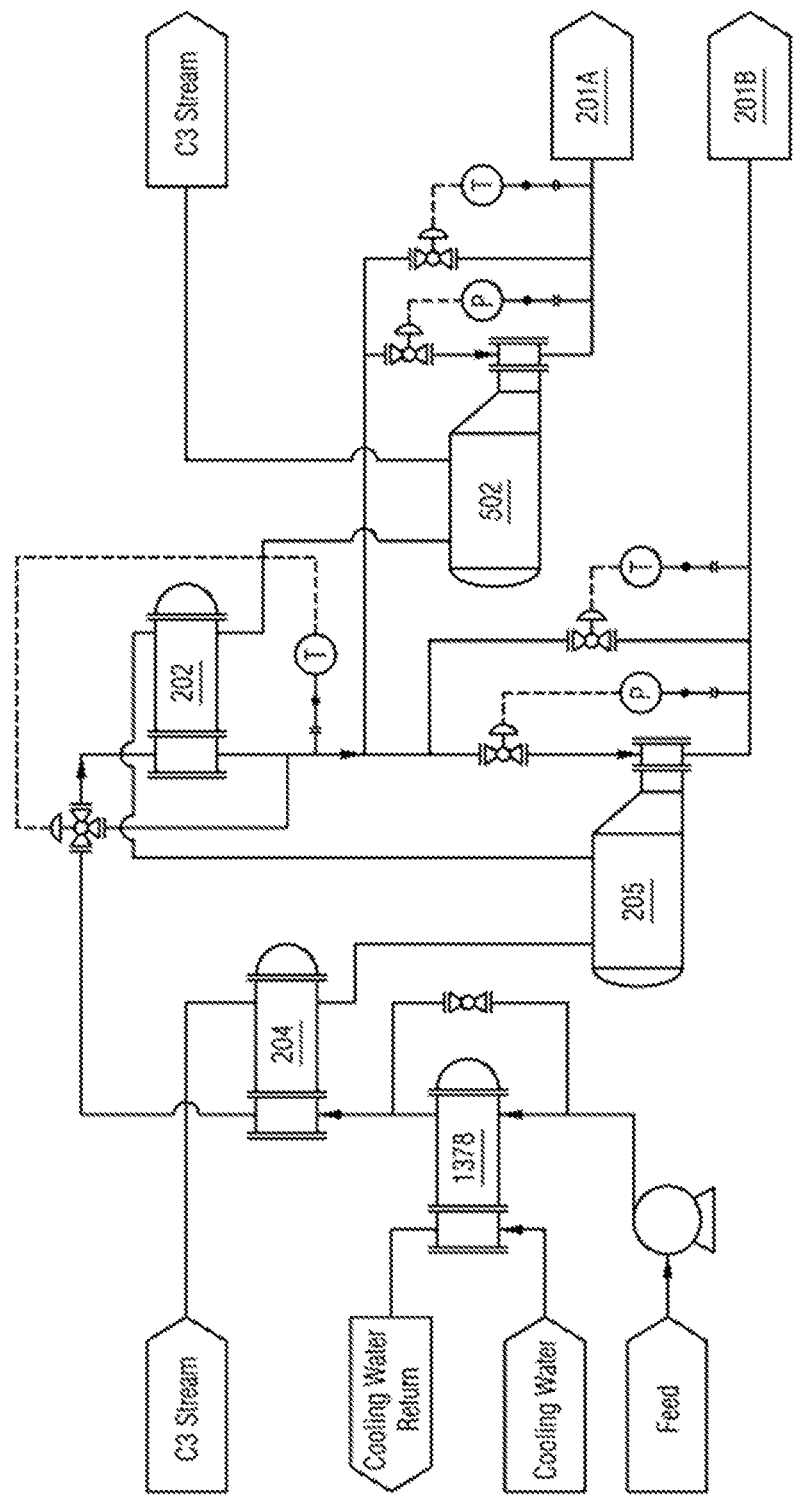

POLYMERIZATION PROCESS

TECHNICAL FIELD OF THE INVENTION

The present invention relates to a polymerization process for forming an ethylene-alpha-olefin polymer and to processes for improving energy utilization, catalyst utilization, and operability of polymerization processes.

BACKGROUND OF THE INVENTION

Polymerization processes producing ethylene-alpha-olefin polymers generally comprise supplying a feed containing ethylene and at least one alpha-olefin and, optionally, a diene in a solvent to a reactor, and then carrying out polymerization in the presence of Ziegler-Natta catalysts or metallocene catalysts to form the polymer. The polymerization of ethylene and alpha-olefin is an exothermic process. Therefore, when the process is carried out in a solution process, for example using a liquid-full continuous flow stirred tank reactor, the heat of polymerization usually needs to be removed, for example, by using cooled solvent.

U.S. Pat. No. 7,119,157 discloses a method of preparing an EP(D)M elastomer, which includes precooling a reactive solvent to a temperature in the range of −80° C. to −100° C. Ethylene, at least one higher alpha-olefin having 3 to 18 carbons, and, optionally, at least one conjugated or non-conjugated diene having 5 to 15 carbons, are polymerized in the presence of the precooled reactive solvent. According to the method, the yield of the EP(D)M elastomer is increased by lowering the reaction temperature even though a conventional preparation device is used unchanged. Further, methods of controlling the yield of the EP(D)M elastomer and of recovering the EP(D)M elastomer are provided.

However, energy utilization and catalyst utilization in this type of process have not been considered extensively, especially in large-scale production plants. For example, where tons per hour of polymers are produced, pre-cooling the feed to −80° C. or lower may result in dramatic energy consumption, especially when increasing the feed rate of monomers, while decreasing the feed temperature in order to improve the yield of the polymer.

Therefore, there is a need for a process for preparing an ethylene-alpha-olefin polymer that provides improved energy utilization, catalyst utilization, and operability of the process, while providing constant attributes of the resulting polymer and without changing the existing polymerization plant.

SUMMARY OF THE INVENTION

Provided herein is a polymerization process that comprises supplying a feed comprising ethylene and at least one alpha-olefin having 3 to 12 carbon atoms in a solvent to a reactor, wherein the feed is supplied to the reactor at a feed temperature and the solvent is supplied at a solvent feed rate; supplying a catalyst to the reactor at a catalyst feed rate, and contacting the feed with the catalyst to form a reaction mixture comprising an ethylene-alpha-olefin polymer.

In one or more embodiments, the feed is supplied to the reactor at a feed temperature of −30° C. or less, or −40° C. or less, but greater than −80° C., and the solvent is provided to the reactor at a solvent feed rate such that the polymer concentration in the reaction mixture is greater than 5 wt %, based on the weight of the reaction mixture.

Also provided herein is a process for improving the energy utilization of a polymerization process, where the polymerization process comprises supplying at a first feed temperature a feed containing ethylene and at least one alpha-olefin having 3 to 12 carbon atoms in a solvent to a reactor, where the solvent is supplied at a first solvent feed rate; supplying a catalyst at a first catalyst feed rate to the reactor; and contacting the feed with the catalyst to form a reaction mixture containing an ethylene-alpha-olefin polymer; and where the process to improve the energy utilization comprises decreasing the feed temperature from a first feed temperature to a second feed temperature, decreasing the solvent feed rate from a first solvent feed rate to a second solvent feed rate, and decreasing the catalyst feed rate from the first catalyst feed rate to a second catalyst feed rate.

In one or more embodiments, the second feed temperature is at least 1° C. less than the first feed temperature, and/or the second feed temperature is in the range of about −80° C. to about −40° C. In one or more embodiments, the first solvent feed rate is decreased to the second solvent feed rate such that the polymer concentration in the reactor mixture may be increased by at least 0.1 wt %, and/or may be increased to greater than 7 wt %, based on the weight of the reaction mixture. In one or more embodiments, the first catalyst feed rate may be decreased to the second catalyst feed rate such that the catalyst efficiency may be increased by at least 10%, and/or the catalyst efficiency may be increased to greater than 400.

In one or more embodiments, the polymerization process further comprises introducing a chain transfer agent to the reactor in an amount of from about 100 ppm to about 500 ppm by weight of the ethylene.

In the processes described herein, by decreasing the feed temperature, decreasing the solvent feed rate, and decreasing the catalyst feed rate, the heat of polymerization may be removed. Energy utilization and catalyst utilization may also be improved, due to less use of catalyst and solvent. Further improvements in energy utilization and catalyst utilization may be realized due to less need for materials used to recover the catalyst residues and solvent, such as steam and water, during recovery of the produced polymers. Preferably, the processes of the present invention may substantially maintain the polymer production rate without changing an existing polymerization plant and substantially maintaining the properties of the polymer being produced.

BRIEF DESCRIPTION OF THE DRAWINGS

The FIGURE illustrates a refrigeration system for precooling the feed before entry into a polymerization reactor.

DETAILED DESCRIPTION OF THE INVENTION

Provided herein are polymerization processes with improved energy utilization. The polymerization process may comprise supplying at a first feed temperature a feed having ethylene and at least one alpha-olefin having 3 to 12 carbon atoms in a solvent to a reactor, wherein the solvent is supplied at a first solvent feed rate; supplying a catalyst at a first catalyst feed rate to the reactor; and contacting the feed with the catalyst to form a reaction mixture containing an ethylene-alpha-olefin polymer. Provided herein are processes to is improve the energy utilization of polymerization processes, where the process comprises decreasing the feed temperature from a first feed temperature to a second feed temperature, decreasing the solvent feed rate from a first solvent feed rate to a second solvent feed rate, and decreasing the catalyst feed rate from a first catalyst feed rate to a second feed rate.

The polymerization process may comprise supplying at a feed temperature of −30° C. or less, or −40° C. or less, but greater than −80° C. a feed containing ethylene and at least one alpha-olefin having 3 to 12 carbon atoms in a solvent to a reactor; and contacting the feed with a catalyst in the reactor to form a reaction mixture containing an ethylene-alpha-olefin-diene polymer, wherein the solvent is provided at a solvent feed rate such that the polymer concentration in the reaction mixture is greater than 5 wt % based on the weight of the reaction mixture.

The term "ethylene-alpha-olefin polymer" as used herein refers to a polymer comprising ethylene-derived units, alpha-olefin-derived units, and optionally, diene-derived units. The term "polymer concentration" as used herein refers to the weight percentage of the desired ethylene-alpha-olefin polymer in the reaction mixture containing the polymer, solvent, and unreacted monomers including ethylene, alpha-olefins, and, optionally, dienes, and may be determined from a ratio of the polymer production rate to the flow rates of solvent and monomers to the reactor.

Useful alpha-olefins include those having from 3 to 20, or from 3 to 12, or from 3 to 8 carbon atoms. Illustrative suitable alpha-olefins are straight and branched chain acyclic and alicyclic alpha-olefins including, propylene, butene-1, pentene-1, hexene-1, octene-1,3-methyl butene-1,4-methyl pentene-1,5,5-dimethyl hexene-1, vinyl cyclopentane, allyl cyclopentane, and vinyl cyclohexane. A preferred alpha-olefin is propylene.

If the ethylene-alpha-olefin polymer comprises a diene, the diene preferably is a non-conjugated diene. Suitable non-conjugated dienes include straight-chain and branched-chain acyclic dienes, such as 1,4-hexadiene, 1,5-hexadiene, 1,6-octadiene, 5-methyl-1,4-hexadiene, 3,7-dimethyl-1,6-octadiene, 3,7-dimethyl-1,7-octadiene, and the mixed isomers of dihydromyrcene and dihydro-ocimene, and single ring alicyclic dienes such as 1,4-cyclohexadiene, 1,5-cyclooctadiene, 1,5-cyclododecadiene, 4-vinyl cyclohexene, 1-allyl-4-isopropylidene cyclohexane, 3-allyl cyclopentene, 4-cyclohexene, and 1-isopropenyl-4-(4-butenyl)cyclohexane. Multi-ring alicyclic fused and bridged ring dienes are also suitable including: tetrahydroindene; methyltetrahydroindene; dicyclopentadiene; bicyclo (2,2,1) hepta-2,5-diene; 2-methyl bicycloheptadiene; and alkenyl, alkylidene, cycloalkenyl and cycloalkylidene norbornenes, such as 5-methylene-2-norbornene, 5-isopropylidene norbornene, 5-(4-cyclopentenyl)-2-norbornene; and 5-cyclohexylidene-2-norbornene. Preferred dienes include 5-ethylidene-2-norbornene, 1,4-hexadiene, and dicyclopentadiene, with 5-ethylidene-2-norbornene being particularly preferred.

Useful solvents may comprise saturated alicyclic and acyclic hydrocarbons having 5 to 10 carbon atoms, aromatic hydrocarbons, and halogenated hydrocarbons that are liquids at the typical conditions used in ethylene-alpha-olefin polymerization reactions. For example, the solvent may comprise n-hexane, isohexane, cyclohexane, 2-methyl pentane, isopentane, decane, benzene, toluene, carbon tetrachloride, and tetrachloroethylene. A preferred solvent is n-hexane, isohexane, or mixture of hexane isomers.

In one or more embodiments, the feed comprising ethylene and alpha-olefins in the solvent may be pre-cooled and supplied at a feed temperature, or at the first feed temperature followed by the decreased second feed temperature, of −30° C. or less, or −35° C. or less, or −40° C. or less, or −45° C. or less, or −50° C. or less, or −55° C. or less, or −60° C. or less. As pre-cooling the feed usually result in consumption of energy, and the lower the feed temperature, the greater the consumption of energy. Therefore, in order to optimize energy utilization, the pre-cooled feed preferably has a temperature of −80° C. or greater, or −70° C. or greater, or −60° C. or greater, or −50° C. or greater. The feed may be pre-cooled and supplied at a feed temperature of between any values as mentioned in this paragraph so long as the lower temperature limit is less than the upper temperature limit, for example, greater than −80° C. and less than −30° C., or greater than −80° C. and less than −40° C., or greater than −80° C. and less than −45° C., or greater than −80° C. and less than −50° C., or greater than −75° C. and less than −40° C., or greater than −70° C. and less than −50° C.

Preferably, the second feed temperature may be less than the first feed temperature by at least 1° C., or by at least 2° C., or by at least 3° C., or by at least 5° C., or by at least 8° C., or by at least 10° C., or by at least 15° C. before being supplied into reactor.

If the feed is pre-cooled to have a first feed temperature and the first feed temperature is further decreased to the second feed temperature, for example, by an additional cooling, the further decrease in feed temperature may be accomplished by using any known method. For example, the further decrease of the feed temperature may be accomplished by changing the types of the cooling agent, such as propylene, ethylene, ammonia, or other CFC or HCFC based refrigerants, and/or lowering the temperature of the cooling agent. Alternatively, the further decrease of the feed temperature may be accomplished by allowing more or even all of the feed to pass through a cooling device, for example, a heat exchanger.

Solvent and monomers including ethylene, alpha-olefins, and, optionally, dienes may be introduced to the reactor in one stream, in which the feed rates of the solvent and different individual monomers may be different. The feed rate of the ethylene, alpha-olefins, and, optional, dienes (or "monomer feed rate") may be within the range of from 1 to 50,000 kg/hr varying from the desired compositions of the polymer, and the feed rate of the solvent ("solvent feed rate") may be within the range of 100 to 500,000 kg/hr. In one embodiment, the solvent is supplied at a first solvent feed rate and then the first solvent feed rate is further decreased to the second solvent feed rate. In this embodiment, both the first solvent feed rate and the second solvent feed rate may be within the above range. Preferably, the solvent feed rate may be decreased from a first solvent feed rate to a second solvent feed rate such that the polymer concentration may be increased by an extent of at least 0.1 wt %, or at least 0.5 wt %, or at least 1 wt %, or at least 1.5 wt %, or at least 2 wt % based on the weight of the reaction mixture formed.

Preferably, the solvent may be supplied at a solvent feed rate, or at the first solvent feed rate followed by the decreased second feed rate such that the polymer concentration in the reaction mixture in the reactor may be 5 wt % or greater, or 5.5 wt % or greater, or 6 wt % or greater, or 6.5 wt % or greater, or 7 wt % or greater, based on the weight of the reaction mixture. For example, the solvent may be supplied at a solvent feed rate, or at the first solvent feed rate followed by the decreased second feed rate, such that the polymer concentration in the reaction mixture is from 5 wt % to 20 wt %, or from 6 wt % to 15 wt %, or from 7 wt % to 15%, based on the weight of the reaction mixture.

The polymerization process is an exothermic reaction and the heat balance is closely related to the feed temperature, types of the solvent, the solvent feed rate, the resulting polymers, and production rate of the polymer. When the polymerization is carried out in a liquid full Continued Flow Stirred-Tank Reactor (CFSTR), the heat balance may be described by the following equation, Equation (1):

$$M_s \times C_p \times (T_r - T_f) = M_p \times \text{Delta } H \quad (1)$$

wherein $M_s$ is the solvent feed rate (lb/hr), $C_p$ is the heat capacity of the solvent (kJ/mol), $T_r$ is the reactor temperature in degrees Fahrenheit (° F.), $T_f$ is the feed temperature in degrees Fahrenheit (° F.), $M_p$ is the polymer production rate and Delta H is the heat of polymerization per unit rate of production. In this equation, the solvent feed rate is limited to the designed capacity of the plant, the heat capacity is related to the types of solvent and the reactor temperature is typically dictated by the impact on monomer conversions and polymer is attributes. Thus, based on this equation, the polymer production rate may be maximized by providing the feed at temperature as low as possible. But as the polymer production rate is also limited by the plant capacity or other equipment in the production process, this equation may suggest that the colder feed temperature may carry the benefit of reducing the solvent feed rate. That may bring direct benefits in terms of energy savings since the recovery, for example, by vaporization of the solvent in the recovery process is the most energy-consuming step.

The process for improving the energy utilization of a polymerization process may comprise decreasing the solvent feed rate from the first solvent feed rate to the second solvent feed rate, and decreasing the feed temperature from the first feed temperature to the second feed temperature in accordance with the following equation, Equation (2):

$$M_{s2} \times (T_r - T_{f2}) \geq M_{s1} \times (T_r - T_{f1}) \quad (2)$$

wherein $M_{s1}$ represents the first solvent feed rate (lb/hr) and $M_{s2}$ represents the second solvent feed rate (lb/hr), $T_r$ represents the reactor temperature in degrees Fahrenheit (° F.), $T_{f1}$ represents the first feed temperature in degrees Fahrenheit (° F.) and $T_{f2}$ represents the second feed temperature in degrees Fahrenheit (° F.). In accordance with Equation (1) and (2), in the process provided herein, the second polymer production rate ($Mp_2$) may be greater than or the same as the first polymer production rate ($Mp_1$) after decrease of the solvent feed rate and decrease of the feed temperature. When the polymer production rate remains the same, energy savings may be achieved by less energy consumption for recovery of the solvent. When the polymer production rate increases, by decreasing the feed temperature and the solvent feed rate, energy saving may be achieved by less energy consumption for recovery of the solvent and/or by less energy consumption for production of per unit weight of polymer even if the total energy consumption remains substantially the same.

It has been found that decreasing the solvent feed rate may result in an increase in reactor residence time. For ethylene-alpha-olefin polymers that possess substantial level of long chain branching ("LCB"), the increased residence time may lead to increased LCB, as expressed by the Mooney Relaxation Area corrected for Mooney (cMLRA), as will be described below.

It has been found that the increase in LCB may be countered through a reduction in catalyst feed to the reactor per unit production rate (or "catalyst feed rate"), which advantageously leads to less utilization of catalyst and increase in catalyst efficiency. The term "catalyst efficiency" as used herein refers to the weight of ethylene-alpha-olefin polymers produced per weight of the catalyst used, and may be evaluated by a ratio of is polymer production rate to the catalyst feed rate. For example, if 300 grams of ethylene-alpha-olefin polymers may be produced using one gram of catalyst, then the catalyst efficiency is determined as 300.

The catalyst may be supplied at a catalyst feed rate. The polymerization process may have a catalyst efficiency of greater than about 300, or greater than about 350, or greater than about 400, or greater than about 450. In a process where the feed temperature is decreased from the first feed temperature to the second feed temperature and the solvent feed rate is decreased from the first solvent feed rate to the second solvent feed rate, the catalyst may be supplied at a first catalyst feed rate and then decreased to a second catalyst feed rate.

Preferably, the first catalyst feed rate may be decreased to the second catalyst feed rate such that the catalyst efficiency may be increased by at least 5%, or by at least 8%, or by at least 15%, or by at least 20%, or by at least 25%, or by at least 30%, or by at least 35%. Preferably, catalyst is supplied to the reactor separately from the feed containing ethylene, at least one alpha-olefin, and, optionally, diene in the solvent.

It has also been found that the increase in Mooney viscosity (ML), as a result of decreased catalyst feed rate, may also be countered through appropriately adjusting the addition of chain transfer agent, such as hydrogen, to the polymerization reactor. In one or more embodiments, where the solvent feed rate is decreased, the chain transfer agent feed rate may be increased from a first chain transfer agent feed rate to a second chain transfer agent feed rate. Preferably, in polymerization processes for preparing an ethylene-propylene-diene polymer ("EPDM") having substantial LCB level, such that the polymers may have a substantial constant ML and cMLRA value, as described above, the amount of chain transfer agent used may be varied to provide the required level of LCB.

Preferably, in order to prevent variation of properties in relation to the LCB level, changes in the molecular weights and molecular weight distributions of the ethylene-alpha-olefin polymers resulting from changes of feed temperature, solvent feed rate, or catalyst feed rate, may also be minimized by the use of a chain transfer agent, such as hydrogen. For example, the amount of chain transfer agent used, if not already being used, may be increased to an amount of from 1 to about 10,000 ppm, or from 1 to 1,000 ppm, or from 1 to 500 ppm, or from 10 to 500 ppm, or from 100 to 500 ppm, based on the weight of ethylene in the reactor.

In a process of improving the energy utilization of a polymerization process, decreasing the feed temperature from the first feed temperature to the second feed temperature, decreasing the solvent feed rate from the first solvent feed rate to the second is feed temperature, and decreasing the catalyst feed rate from the first catalyst feed rate to the second catalyst feed rate, may be accomplished simultaneously in one embodiment or may be accomplished separately in any order in another embodiment.

Catalysts useful in the polymerization processes described herein may comprise a Ziegler-Natta catalyst. Any Ziegler-Natta catalyst known in the art may be useful. Such catalysts include compounds of the transition metals of Groups 4 to 6 of the Periodic Table of Elements. Catalysts comprising vanadium and titanium compounds are preferred. Suitable vanadium compounds include compounds having the general formula $VO_zX_t$ wherein z has a value of 0 to 1, t has a value of 2, 3 or 4, and the sum of z and t is 4 or less and X is independently selected from the group consisting of halogens having an atomic number equal to or greater than 17, acetylacetonates (AcAc), haloacetylacetonates, alkoxides and haloalkoxides. Non-limiting examples of suitable catalysts include: $VOCl_3$, $VCl_4$, $VO(OC_2H_5)_3$, $VO(AcAc)_2$, $VOCl_2(OC_2H_5)$, $VOCl_2(OC_4H_9)$, $V(AcAc)_3$ and $VOCl_2(AcAc)$, where (AcAc) is an acetyl acetonate. Suitable titanium compounds include $TiCl_3$, $TiCl_4$, and compounds of the formula $Ti(OR)_4$ wherein R is an acyclic or alicyclic monovalent hydrocarbon radical of one to twelve carbon atoms. Examples of such titanium alkoxides include tetrabutyl titanate, tetraisopropyl titanate, and tetra (2-ethyl hexyl) titanate. Preferred catalyst systems employ $VCl_4$ or $VOCl_3$, in combination with either $Ti(OC_4H_9)_4$ or $VO(OC_2H_5)_3$.

An organoaluminum compound may be useful as a cocatalyst used with the Ziegler-Natta catalyst. Suitable cocatalysts include compounds of the formula $AlR'_mX'_n$ wherein R' is a monovalent hydrocarbon radical selected from the group consisting of $C_1$-$C_{12}$ alkyl, alkylaryl, and cycloalkyl radicals, m is a number from 1 to 3, X' is a halogen having an atomic number equal to or greater than 17 (Cl, Br and I), and the sum of m and n is equal to three, e.g., $Al(C_2H_5)_3$, $Al(C_2H_5)_2Cl$, $Al(i-C_4H_9)_2Cl$, $Al(i-C_4H_9)_3$ and $Al(C_2H_5)Cl_2$. Mixtures of such compounds may also be used. Preferred cocatalysts are $Al(C_2H_5)_2Cl$ and $Al_2(C_2H_5)_3Cl_3$.

Catalysts useful in the polymerization processes described herein may comprise metallocene catalysts, or so-called single site catalysts. The term "metallocene" herein is defined to contain one or more cyclopentadienyl moiety in combination with a transition metal of the Periodic Table of Elements. These generally contain a transition metal of Groups 3 to 10 of the Periodic Table of Elements and at least one ancillary ligand that remains bonded to the transition metal during polymerization. Preferably, the transition is metal is used in a cationic state and stabilized by a cocatalyst or activator. Especially preferred are metallocenes of Group 4 of the Periodic Table of Elements such as titanium, hafnium, or zirconium which are used in polymerization in the mono-valent cationic state and have one or two ancillary ligands as described in more detail hereafter.

Preferably, the metallocene catalyst is a bulky ligand transition metal catalyst. The term "bulky ligand" contains a multiplicity of bonded atoms, preferably carbon atoms, forming a group, which may be cyclic with one or more heteroatoms. The bulky ligand may be metallocene-type cyclopentadienyl derivative, which may be mono- or poly-nuclear. One or more bulky ligands may be bonded to the transition metal atom. It is believed that the bulky ligand remains in position during the course of polymerization to provide a homogenous polymerization effect. Other ligands may be bonded or coordinated to the transition metal, preferably detachable by a cocatalyst or activator, such as a hydrocarbyl or halogen-leaving group. Preferably, the transition metal atom is a Group 4, 5 or 6 transition metal of the Periodic Table of Elements. More preferably, the transition metal atom comprises a Group 4 transition metal atom. Useful metallocene catalysts may be those as described in WO 99/41294, the disclosure of which is incorporated herein by reference.

The metallocene catalyst may be used with a cocatalyst. Useful cocatalysts may comprise an alumoxane, preferably a methylalumoxane having an average degree of oligomerization of from 4 to 30 as determined by vapor pressure osmometry. Alumoxane may be modified to provide solubility in linear alkanes or be used in slurry, but may be generally used from a toluene solution. Such solutions may include unreacted trialkyl aluminum and the alumoxane concentration may be generally indicated as mol Al per liter, which figure includes any trialkyl aluminum which has not reacted to form an oligomer. The alumoxane, when used as cocatalyst, may be generally used in molar excess, at a mol ratio of 50 or more, preferably 100 or more, and preferably 1000 or less, preferably 500 or less, relative to the transition metal.

A metallocene may be also used with a cocatalyst which may be a non-coordinating anion (or "NCA"). The term "non-coordinating anion" as used herein includes weakly coordinated anions and the coordination may be sufficiently weak in any event as evidenced by the progress of polymerization to permit the insertion of the unsaturated monomer component. The non-coordinating anion may be supplied and reacted with the metallocene in any of the manners described in the art. The non-coordinating anion may be a halogenated, tetra-aryl-substituted Group 10 to 14 non-carbon element-based anion, especially those containing fluorine groups substituted for hydrogen atoms on the aryl groups, or on alkyl substituents on those aryl groups. The non-coordinating anion, when used as cocatalysts, may be used in approximately equimolar amounts relative to the transition metal component, such as at least 0.25, or at least 0.5, or at least 0.8 and less than 4, or less than 2, or less than 1.5.

The reaction conditions including catalyst, temperature, and pressure in the polymerization process may be varied. Suitable temperature for polymerization of ethylene-alpha-olefin polymers may be within the range of from −50 to 150° C., or from 0 to 100° C., or from 10 to 70° C. Suitable pressure for polymerization of ethylene-alpha-olefin polymers may vary from the temperature in the polymerization reactor. In general, the pressure may be maintained at a level sufficient to maintain the solvent in a liquid phase. Preferred pressure to maintain the solvent in a liquid phase may be from 20 to 200 psig (or 0.2 to 1.5MPa).

Preferably, the ethylene-alpha-olefin polymer may comprise from 10 wt % to 90 wt %, or from 15 wt % to 80 wt %, or from 40 wt % to 80 wt %, of ethylene-derived units and from 90 wt % to 10 wt %, or from 85 wt % to 20 wt %, or from 60 wt % to 20 wt % of alpha-olefin-derived units, based on the weight of the ethylene-alpha-olefin polymer. Preferably, the amount of the diene-derived units may be of from 0.1 wt % to 20 wt %, or from 0.1 wt % to 15 wt %, or from 1 wt % to 15 wt %, or from 3 wt % to 12 wt %, based on the weight of the ethylene-alpha-olefin polymer. Different feed rates of ethylene, alpha-olefins, and optional dienes may be useful to the reaction system to obtain desired compositional diversity. The feed rates may also vary from different production rates of the ethylene-alpha-olefin polymer, and/or even the feed temperature.

Preferably, the ethylene-alpha-olefin polymer may have a Mooney viscosity measured at (1+4 @ 125° C.) by ASTM-1646 between any lower limit of 1, 2, 5, 8, 10, and 15 and any upper limit of 100, 90, 85, 80, and 75. For example, the ethylene-alpha-olefin polymer may have a Mooney viscosity of from about 5 to 90, or from 8 to 85, or from 10 to 80, or from 15 to 75.

The ethylene-alpha-olefin polymer may comprise a substantial level of long chain branching ("LCB"). The level of long chain branching may be characterized by Mooney relaxation of the polymer because a relaxation time is strongly dependent on the presence of high molecular weight species built-up by long chain branching of the polymer and high molecular weight macromolecules relax slowly thus leading to a large area under the Mooney Relaxation Curve ("MLRA"), which may be measured according to ASTM D 1646 (1+4 @ 125° C.) using a MV 2000 E (manufactured by Alpha Systems) or equivalent equipment is capable of measuring Mooney relaxation. MLRA may be expressed by measuring the Mooney stress relaxation starting 1 second after the rotor is stopped and continuing to collect measurements up to 100 seconds of stress relaxation time. MLRA may be calculated according to the following equation, Equation (3):

$$MLRA = [100^{(a+1)} - 1] \times [k/(a+1)] \quad (3)$$

in which "a" and "k" are respectively the slope and intercept of the least square regression line of log(Mooney torque) versus log(relaxation time) measured between 1 and 100 seconds relaxation time and using equipment build-in data sampling protocol.

As MLRA is measured after the Mooney viscosity measurement according to ASTM D 1646 (1+4 @ 125° C.) and the starting point of the exponential relaxation curve is dictated by the ML value accordingly, it is closely tied with the Mooney viscosity. A corrected MLRA for Mooney ("cMLRA") may substantially eliminate the Mooney viscosity dependence and may, thus, be used to express the LCB level of the ethylene-alpha-olefin polymers. Correction of MLRA for Mooney viscosity may be made by approximately fitting a line for all data points of MLRA and ML for a specific grade of ethylene-alpha-olefin polymer to determine the slope used to calculate the cMLRA from measured MLRA; and then correcting the MLRA using the measured ML of the specific grade of polymer and the slope to calculate the cMLRA.

The ethylene-alpha-olefin polymers may have a MLRA, as measured by ASTM D 1646 (1+4 @ 125° C.), of from 50 to 1000, or from 80 to 800, or from 100 to 500, or from 150 to 300. The ethylene-alpha-olefin polymers may have a cMLRA of less than 2000, or from 10 to 1000, or from 30 to 800, or from 50 to 500, or from 100 to 350.

After polymerization in reactor(s), a de-catalyzing process may be carried out to remove any catalyst residues that remain in the reaction mixture. Any known de-catalyzing process may be useful. For example, a deashing step may be used to terminate the reaction and to remove any catalyst residues. In such embodiments, the reaction mixture containing ethylene-alpha-olefin polymer, solvent, unreacted monomers, and catalyst residues coming out from the reactor may be mixed with a quench agent, such as a hydroxide material, for example, cooling water, in an amount of 50 to 150 vol %, or 60 to 80 vol %, and an emulsifier in an amount of 0.001-0.01 wt %, based on the amount of the reaction mixture. Subsequently, the hydroxide layer is removed by the difference in specific gravity, whereby the catalyst residues dissolved in the hydroxide layer is removed. The deashing step may be carried out in multiple stages to remove the catalyst residues as much as possible.

A polymer stream obtained after the deashing step may include solid polymer, unreacted monomers, and the solvent. Recovery of the solvent may be carried out by any known method. In one or more preferred embodiments, the recovery of the polymer may be carried out in a steam stripping process, in which the polymer stream, after the deashing step and recovery of unreacted monomers, is transferred into a stripper maintained at a temperature at or above about 95° C. using steam to volatilize the solvent. In some embodiments, the recovery of the polymer may be carried out by a "direct drying process", in which the polymer stream may be recovered by thermal treatment, pressure reduction using a flash vessel, and then thermal drying (extrusion).

It is believed in the polymerization process of the present invention, reducing the solvent feed rate at a given polymer production rate may lead to an increase in polymer concentration and therefore, an increase in the cement viscosity. The term "cement viscosity" as used herein refers to viscosity of the reaction mixture. The increase in cement viscosity with polymer concentration is a function of polymer molecular weight (Mooney viscosity) and has important consequences to the operability of the plant such as in the ability to remove the catalyst residues (deashing) after the polymerization is stopped downstream of the reactor with a quench agent. It is believed the deashing step is a mass transfer controlled process where the transfer of the catalyst residues from the hydrocarbon phase to the aqueous phase is diffusion controlled. This may be typically accomplished in a counter current staged flow process in agitated vessels. The number of stages used will dictate the consumption of energy to remove the catalyst residues from the polymer at a viscosity.

Although additional pre-cooling of the feed may initially increase consumption of energy, there is still a net reduction in energy consumption due to the energy savings in the solvent recovery process, which could be the most energy-consuming process in separation or recovery of the ethylene-alpha-olefin polymers of the present invention, is factored into consideration. In the meantime, the reduced catalyst usage and increased catalyst efficiency results in lower catalyst cost as well as reduction in number of deashing stages required to reach low catalyst residues level in the polymer and thus accomplished higher energy utilization.

A better understanding of the present invention may be obtained in light of the following example which are set forth for illustration, but are not to be constructed to limit the present invention.

EXAMPLES

Polymerizations in Examples 1 and 2 were conducted according to the present invention in an existing plant for production of Product A, an EPDM comprising about 76 wt % of ethylene-derived units, about 3.3 wt % of 5-ethylidene-2-norbornene (ENB)-derived units, with the balance being propylene-derived units, based on the weight of the EPDM. The EPDM has a target Mooney viscosity (ML) of 24. The feed comprising ethylene, propylene, and 5-ethylidene-2-norbornene (ENB) in isohexane was rigorously purified prior to entry into a continued flow stirred reactor for polymerization to remove polar impurities that may act as catalyst poisons. The catalyst and cocatalyst, supplied separately from the feed, were vanadium tetrachloride (VCl4) and ethy-laluminum sesquichloride (AlEt2Cl/AlEtCl2). The FIGURE shows the refrigeration system for pre-cooling the feed. In the FIGURE, elements 1378, 202, 204, 205, and 502 represent heat exchangers as a cooling device. A propylene stream was used as cooling agent in the heat exchangers 204, 202, 205, and 502, and a cooling water stream was used in heat exchanger 1378.

In Example 1, the feed was pre-cooled to −35° C. by the refrigeration system as shown in the FIGURE before entry into the reactor. In Example 2, the feed temperature was decreased from the first feed temperature of −35° C. to the second feed temperature of −43° C. by removing constraint in the control system around the heat exchangers 202 and 205 to allow more of the feed flow through the heat exchangers before entry into the reactors 201A and 201B. The solvent feed rate was decreased from the first solvent feed rate in Example 1 to the second solvent feed rate of Example 2, the catalyst feed rate was decreased from the first catalyst feed rate in Example 1 to the second catalyst feed rate in Example 2, but the monomer feed rates in Example 2 remained the same as in in Example 1. Some process conditions are shown in Table 1.

After polymerization, a reaction mixture was formed and comprised of the EPDM, catalyst residues, solvent and unreacted monomers. Each reaction mixture of Example 1 and Example 2 was then separated by the following operation. The reaction mixture was discharged from the reactor. Cooling water was then added into the reaction. Then the aqueous phase was separated from the reaction mixture to remove the catalyst residues. Cooling water may be added and separated in multiple times until the reaction mixture was substantially absent from the catalyst residues. Following the deashing process the reaction mixture was transferred into a stripper, which was maintained at a temperature of about 95° C. or higher using steam to volatilize the hexane isomers.

TABLE 1

Operation Conditions

| Operating Conditions | Example 1 | Example 2 |
|---|---|---|
| Feed temperature (° F.) | −32° F. (−35° C.) | −44° F. (−43° C.) |
| Reactor temperature (° F.) | 149° F. (65° C.) | 149° F. (65° C.) |
| Solvent (lb/hr) | 280,000 (127,000 kg/hr) | 236,000 (107,000 kg/hr) |
| Catalyst (lb/hr) | 59 | 49 |
| H2/Ethylene (weight ratio, ppm) | 150 | 200 |
| Polymer concentration (%) | 6.65 | 7.95 |
| Catalyst efficiency | 330 | 450 |
| Deashing stages | 6 | 3 |

It may be seen from Table 1 that Example 2, compared with Example 1, had is increased polymer concentration because of the decreased solvent feed rate and increased catalyst efficiency because of the decrease of the catalyst feed rate. The deashing stages were decreased from 6 to 3. These changes resulted in significant savings of use of steams for separating solvent from the reaction mixture. Other savings of energy utilization and raw material included decreased consumption of cooling water, electricity and catalyst. Compared with the process of Example 1, the annualized savings in utilities and raw materials according to the process of Example 2 are shown in Table 2.

TABLE 2

Annualized Utility/Raw Material Savings

| Utility/Raw Material | Annualized Savings |
|---|---|
| Stream | 2,524 MBTU/ton |
| Cooling water | 19 Mgal/ton |
| Electricity | 30,602 Kw-h/ton |
| Catalyst | 1,782 lb/ton |

In each of Examples 1 and 2, fifteen samples of Product A were obtained and measured for viscosity, MLRA and cMLRA. Based on the data of MLRA and ML as measured, the slope for calculating cMLRA from MLRA was estimated from the fit to the measured data as MLRA=14.827×ML−179.1, and $R^2$=0.9721. cMLRA of each sample at 24 ML (target ML of the Product A) was then calculated from measured MLRA using the slope. The results are shown in Table 3. Mooney viscosities and Mooney Stress Relaxation of products were measured by ASTM method D-1646 at (1+4 @ 125° C.), as described herein.

TABLE 3

Properties of Samples of Product A

| Example No. | Mooney viscosity (ML) | MLRA | cMLRA |
|---|---|---|---|
| 1.1 | 25.0 | 198.4 | 184 |
| 1.2 | 24.2 | 182.8 | 180 |
| 1.3 | 25.0 | 198.2 | 184 |
| 1.4 | 25.2 | 194.9 | 177 |
| 1.5 | 26.1 | 204.8 | 174 |
| 1.6 | 26.0 | 203.5 | 174 |
| 1.7 | 24.9 | 189.2 | 176 |
| 1.8 | 24.9 | 184.5 | 171 |
| 1.9 | 25.1 | 181.1 | 165 |
| 1.10 | 25.5 | 192.7 | 171 |
| 1.11 | 24.5 | 191.4 | 184 |
| 1.12 | 24.8 | 182.8 | 171 |
| 1.13 | 24.6 | 177.6 | 169 |
| 1.14 | 25.2 | 189.2 | 172 |
| 1.15 | 25.9 | 197.6 | 170 |
| 2.1 | 24.6 | 180.5 | 172 |
| 2.2 | 25.0 | 192.5 | 178 |
| 2.3 | 23.9 | 184.4 | 186 |
| 2.4 | 23.3 | 169.6 | 180 |
| 2.5 | 23.8 | 176.1 | 179 |
| 2.6 | 22.8 | 162.2 | 180 |
| 2.7 | 23.0 | 170.7 | 185 |
| 2.8 | 24.1 | 173.6 | 172 |
| 2.9 | 23.9 | 169.7 | 171 |
| 2.10 | 23.6 | 164.2 | 170 |
| 2.11 | 23.7 | 169.2 | 174 |
| 2.12 | 23.2 | 164.2 | 176 |
| 2.13 | 24.1 | 170.2 | 169 |
| 2.14 | 24.0 | 182.5 | 183 |
| 2.15 | 24.0 | 171.3 | 171 |

It may be seen from Table 3 that the Mooney viscosity and cMLRA, representing long chain branching level of the samples were maintained in substantially the same range among the samples of Examples 1 and 2. That is, in the process of Example 2 the energy utilization was improved and the product attributes were maintained at the same time.

Having described the various aspects of the present invention herein, further specific embodiments of the invention include those set forth in the following paragraphs.

Paragraph 1. A polymerization process, comprising: supplying a feed containing ethylene and at least one alpha-olefin having 3 to 12 carbon atoms in a solvent to a reactor, where the feed is supplied at a temperature in the range of about −30° C. to about −80° C.; and contacting the feed with a catalyst in the reactor to form a reaction mixture containing an ethylene-alpha-olefin-diene polymer, wherein the solvent is provided at a solvent feed rate such that the polymer concentration in the reaction mixture is greater than 5 wt % based on the weight of the reaction mixture.

Paragraph 2. The process of Paragraph 1, wherein the feed temperature is −40° C. or less.

Paragraph 3. The process of Paragraph 1 or 2, wherein the polymer concentration is greater than 7 wt % based on the weight of the reaction mixture.

Paragraph 4. The process of any of Paragraphs 1 to 3, comprising supplying the catalyst at a catalyst feed rate such that the catalyst efficiency is greater than 400.

Paragraph 5. The process of any of Paragraphs 1 to 4, wherein the catalyst comprises a transition metal of Groups 4-6 in the Periodic Table of Elements.

Paragraph 6. The process of Paragraph 5, wherein the transition metal is vanadium or titanium.

Paragraph 7. The process of any of Paragraphs 1 to 6, wherein the process is carried out in the presence of a chain transfer agent in an amount of from 100 to 500 ppm based on the weight of the ethylene.

Paragraph 8. The process of any of Paragraphs 1 to 7, wherein the solvent comprises at least one of alicyclic and acyclic hydrocarbons having 5 to 10 carbon atoms, aromatic hydrocarbons, aromatic hydrocarbons, and halogenated hydrocarbons.

Paragraph 9. The process of any of Paragraphs 1 to 8, wherein the solvent is n-hexane, isohexane, or mixture of hexane isomers.

Paragraph 10. The process of any of Paragraphs 1 to 9, wherein the ethylene-alpha-olefin polymer has a Mooney viscosity (ML 1+4, 125° C.) as measured by ASTM-D 1646 of from about 10 to 100.

Paragraph 11. The process of any of Paragraphs 1 to 10, wherein the ethylene-alpha-olefin polymer has a MLRA of from about 50 to about 1000, where MLRA is the area under the Mooney Relaxation Curve measured according to ASTM D 1646 (1+4 @ 125° C.).

Paragraph 12. The process of any of Paragraphs 1 to 11, wherein the ethylene-alpha-olefin polymer has a cMLRA of less than 2000, where cMLRA is MLRA corrected for Mooney viscosity and MLRA is the area under the Mooney Relaxation Curve measured according to ASTM-D 1646 (1+4 @ 125° C.).

Paragraph 13. The process of any of Paragraphs 1 to 12, wherein the ethylene-alpha-olefin polymer comprises about 10 wt % to about 90 wt % of ethylene-derived units, about 90 wt % to about 10 wt % of the at least one alpha-olefin-derived units based on the total weight of the polymers.

Paragraph 14. The process of any of Paragraphs 1 to 13, wherein the polymers comprises about 0.1 wt % to about 15 wt % of the diene-derived units based on the total weight of the polymers.

Paragraph 15. The process of any of Paragraphs 1 to 14, wherein the feed comprises ethylene, propylene, and ethylidene norbornene.

Paragraph 16. A process for improving the energy utilization of a polymerization process, wherein the polymerization process comprises supplying at a first feed temperature a feed containing ethylene and at least one alpha-olefin having 3 to 12 carbon atoms in a solvent to a reactor, where the solvent is supplied at a first solvent feed rate; supplying a catalyst at a first catalyst feed rate to the reactor; and contacting the feed with the catalyst to form a reaction mixture containing an ethylene-alpha-olefin polymer; and wherein the process for improving the energy utilization comprises: decreasing the first feed temperature to a second feed temperature; decreasing the first solvent feed rate to a second solvent feed rate; and decreasing the first catalyst feed rate to a second catalyst feed rate.

Paragraph 17. The process of Paragraph 16, wherein the second feed temperature is at least 1° C. less than the first feed temperature.

Paragraph 18. The process of Paragraph 16 or 17, wherein the second feed temperature is −40° C. or less but greater than −80° C.

Paragraph 19. The process of any of Paragraphs 16 to 18, wherein decreasing the first solvent feed rate to the second solvent feed rate increases the polymer concentration in the reaction mixture by at least 1 wt %.

Paragraph 20. The process of any of Paragraphs 16 to 19, wherein decreasing the first solvent feed rate to the second solvent feed rate obtains the polymer concentration in the reaction mixture of greater than 7 wt %.

Paragraph 21. The process of any of Paragraphs 16 to 20, wherein decreasing the first solvent feed rate to the second solvent feed rate follows to equation:

$$M_{s2} \times (T_r - T_{f2}) \geq M_{s1} \times (T_r - T_{f1})$$

wherein $M_{s1}$ represents the first solvent feed rate and $M_{s2}$ represents the second solvent feed rate, $T_r$ represents the reactor temperature, $T_{f1}$ represents the first feed temperature and $T_{f2}$ represents the second feed temperature.

Paragraph 22. The process of any of Paragraphs 16 to 21, wherein decreasing the first catalyst feed rate to the second catalyst feed rate increases the catalyst efficiency by at least 10%.

Paragraph 23. The process of any of Paragraphs 16 to 22, decreasing the first catalyst feed rate to the second catalyst feed rate obtains the catalyst efficiency of greater than 400.

Paragraph 24. The process of any of Paragraphs 16 to 23, comprising supplying a chain transfer agent at a first chain transfer agent rate to the reactor and increasing the first chain transfer agent feed rate to a second chain transfer agent feed rate.

Paragraph 25. The process of any of Paragraphs 16 to 24, wherein decreasing the first chain transfer agent feed rate to the second chain transfer agent feed rate obtains the amount of the chain transfer agent in the reactor of from 100 ppm to 500 ppm by the weight of the ethylene.

Paragraph 26. A polymerization process, comprising: supplying at a first feed temperature of greater than −80° C. and less than −30° C. a feed containing ethylene, at least one alpha-olefin having 3 to 12 carbon atoms and a diene in a solvent to a reactor, where the solvent is supplied at a first solvent feed rate; supplying a catalyst at a first catalyst feed rate to the reactor; and contacting the feed with the catalyst to form a reaction mixture containing an ethylene-alpha-olefin-diene polymer, wherein the process further comprises: decreasing the first feed temperature to a second feed temperature, and the second feed temperature is at least 5° C. less than the first feed temperature; decreasing the first solvent feed rate to a second solvent feed rate to obtain the polymer concentration in the reaction mixture of greater than 7 wt %; and decreasing the first catalyst feed rate to a second catalyst feed rate to increase the catalyst efficiency by at least 10%.

All patents, patent applications, test procedures, priority documents, articles, publications, manuals, and other documents cited herein are fully incorporated by reference for all jurisdictions in which such incorporation is permitted. All numerical values are "about" or "approximately" the indicated value, and take into account experimental error and variations that would be expected by a person having ordinary skill in the art. When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the invention pertains.

What is claimed is:

1. A polymerization process, comprising:
    supplying a feed containing ethylene and at least one alpha-olefin having 3 to 12 carbon atoms in a solvent to a reactor, where the feed is supplied at a temperature in the range of about −80° C. to about −30° C.; and
    contacting the feed with a catalyst in the reactor to form a reaction mixture containing an ethylene-alpha-olefin polymer, wherein the solvent is provided at a solvent feed rate such that the polymer concentration in the reaction mixture is greater than 5 wt % based on the weight of the reaction mixture;

wherein the catalyst is supplied at a catalyst feed rate such that the catalyst efficiency is greater than 400.

2. The process of claim 1, wherein the feed temperature is less than or equal to −40° C.

3. The process of claim 1, wherein the polymer concentration is greater than 7 wt % based on the weight of the reaction mixture.

4. The process of claim 1, wherein the catalyst comprises a transition metal of Groups 4 to 6 in the Periodic Table of Elements.

5. The process of claim 1, wherein the process is carried out in the presence of a chain transfer agent in an amount of from 100 to 500 ppm based on the weight of the ethylene.

6. The process of claim 1, wherein the solvent comprises at least one of alicyclic and acyclic hydrocarbons having 5 to 10 carbon atoms, aromatic hydrocarbons, aromatic hydrocarbons, and halogenated hydrocarbons.

7. The process of claim 1, wherein the solvent is n-hexane, isohexane, or mixture of hexane isomers.

8. The process of claim 1, wherein the ethylene-alpha-olefin polymer has a Mooney viscosity (ML 1+4, 125° C.) as measured by ASTM-D 1646 of from 10 to 100.

9. The process of claim 8, wherein the ethylene-alpha-olefin polymer has a MLRA of from 50 to 1000, where MLRA is the area under the Mooney Relaxation Curve measured according to ASTM-D 1646 (1+4 @ 125° C.).

10. The process of claim 8, wherein the ethylene-alpha-olefin polymer has a cMLRA of less than 2000, where cMLRA is MLRA corrected for Mooney viscosity and MLRA is the area under the Mooney Relaxation Curve measured according to ASTM-D 1646 (1+4 @ 125° C.).

11. The process of claim 1, wherein the ethylene-alpha-olefin polymer comprises 10 wt % to 90 wt % of ethylene-derived units and 90 wt % to 10 wt % of the at least one alpha-olefin-derived units based on the total weight of the polymer.

12. The process of claim 11, wherein the polymer further comprises about 0.1 wt % to about 15 wt % of the diene-derived units based on the total weight of the polymer.

13. The process of claim 1, wherein the feed comprises ethylene, propylene, and ethylidene norbornene.

14. A process for improving the energy utilization of a polymerization process, wherein the polymerization process comprises supplying at a first feed temperature a feed containing ethylene and at least one alpha-olefin having 3 to 12 carbon atoms in a solvent to a reactor, where the solvent is supplied at a first solvent feed rate; supplying a catalyst at a first catalyst feed rate to the reactor; and contacting the feed with the catalyst to form a reaction mixture containing an ethylene-alpha-olefin polymer; and wherein the process to improve the energy utilization comprises:

decreasing the first feed temperature to a second feed temperature;

decreasing the first solvent feed rate to a second solvent feed rate; and decreasing the first catalyst feed rate to a second catalyst feed rate.

15. The process of claim 14, wherein the second feed temperature is at least 1° C. less than the first feed temperature.

16. The process of claim 14, wherein the second feed temperature is −40° C. or less but greater than −80° C.

17. The process of claim 14, wherein decreasing the first solvent feed rate to the second solvent feed rate increases the polymer concentration in the reaction mixture by at least 1 wt %.

18. The process of claim 14, wherein decreasing the first solvent feed rate to the second solvent feed rate obtains the polymer concentration in the reaction mixture of greater than 7 wt %.

19. The process of claim 14, wherein decreasing the first solvent feed rate to the second solvent feed rate follows to equation:

$$M_{s2} \times (T_r - T_{f2}) \geq M_{s1} \times (T_r - T_{f1})$$

wherein $M_{s1}$ represents the first solvent feed rate and $M_{s2}$ represents the second solvent feed rate, $T_r$ represents the reactor temperature, $T_{f1}$ represents the first feed temperature and $T_{f2}$ represents the second feed temperature.

20. The process of claim 14, wherein decreasing the first catalyst feed rate to the second catalyst feed rate increases the catalyst efficiency by at least 10%.

21. The process of claim 14, wherein decreasing the first catalyst feed rate to the second catalyst feed rate obtains the catalyst efficiency of greater than 400.

22. The process of claim 14 comprising supplying a chain transfer agent at a first chain transfer agent rate to the reactor and increasing the first chain transfer agent feed rate to a second chain transfer agent feed rate.

23. The process of claim 22, wherein the second chain transfer agent feed rate introduces chain transfer agent to the reactor in an amount of from 100 ppm to 500 ppm by the weight of the ethylene.

24. A polymerization process, comprising:

supplying at a first feed temperature of greater than −80° C. and less than −30° C. a feed containing ethylene, at least one alpha-olefin having 3 to 12 carbon atoms and a diene in a solvent to a reactor, where the solvent is supplied at a first solvent feed rate;

supplying a catalyst at a first catalyst feed rate to the reactor; and contacting the feed with the catalyst to form a reaction mixture containing an ethylene-alpha-olefin-diene polymer, wherein the process further comprises:

decreasing the first feed temperature to a second feed temperature, and the second feed temperature is at least 5° C. less than the first feed temperature;

decreasing the first solvent feed rate to a second solvent feed rate to obtain the polymer concentration in the reaction mixture of greater than 7 wt %; and decreasing the first catalyst feed rate to a second catalyst feed rate to increase the catalyst efficiency by at least 10%.

* * * * *